US007011633B2

(12) United States Patent
Strandberg

(10) Patent No.: US 7,011,633 B2
(45) Date of Patent: Mar. 14, 2006

(54) BLOOD FLOW MEASURING APPARATUS

(75) Inventor: Hans Strandberg, Sundbyberg (SE)

(73) Assignee: St. Jude Medical AB, Jarfalla (SE)

( * ) Notice: Subject to any disclaimer, the term of this patent is extended or adjusted under 35 U.S.C. 154(b) by 73 days.

(21) Appl. No.: 10/477,545

(22) PCT Filed: Jan. 10, 2002

(86) PCT No.: PCT/SE02/00036

§ 371 (c)(1),
(2), (4) Date: Nov. 13, 2003

(87) PCT Pub. No.: WO02/096285

PCT Pub. Date: Dec. 5, 2002

(65) Prior Publication Data
US 2004/0147967 A1 Jul. 29, 2004

(30) Foreign Application Priority Data
May 31, 2001 (SE) .................................. 0101917

(51) Int. Cl.
*A61B 5/02* (2006.01)
(52) U.S. Cl. ....................... 600/505; 600/504
(58) Field of Classification Search .......... 73/861, 73/861.01–861.03, 861.08; 600/504–507, 600/381; 324/71.1, 306, 600; 607/9, 17–24, 607/28
See application file for complete search history.

(56) References Cited

U.S. PATENT DOCUMENTS

| 3,734,083 | A | * | 5/1973 | Kolin | 600/505 |
| 4,721,115 | A | | 1/1988 | Owens | |
| 4,785,823 | A | | 11/1988 | Eggers et al. | |
| 4,805,621 | A | * | 2/1989 | Heinze et al. | 600/547 |
| 5,501,662 | A | * | 3/1996 | Hofmann | 604/20 |
| 5,598,847 | A | | 2/1997 | Renger | |
| 5,602,342 | A | | 2/1997 | Strandberg | |
| 5,799,350 | A | * | 9/1998 | Ferek-Petric et al. | 607/17 |
| 6,015,393 | A | * | 1/2000 | Hovland et al. | 600/587 |
| 6,053,873 | A | * | 4/2000 | Govari et al. | 600/505 |
| 6,115,633 | A | * | 9/2000 | Lang et al. | 607/17 |
| 6,360,123 | B1 | * | 3/2002 | Kimchi et al. | 600/547 |
| 6,413,223 | B1 | * | 7/2002 | Yang et al. | 600/485 |
| 6,442,413 | B1 | * | 8/2002 | Silver | 600/345 |

FOREIGN PATENT DOCUMENTS

WO   WO 82/00581   3/1982

* cited by examiner

Primary Examiner—Max F. Hindenburg
Assistant Examiner—Patricia Mallari
(74) Attorney, Agent, or Firm—Schiff Hardin LLP

(57) ABSTRACT

A blood flow measuring apparatus has a measuring electrode and a counter-electrode adapted to be brought into contact with the blood of a patient. A measuring unit measures a voltage or a current between the measuring electrode and the counter-electrode and determines the flow of blood therefrom. The measuring electrode is ring-shaped and sized to fit within a blood vessel in the body of the patient. An inner surface of the ring-shaped electrode forms an active measuring electrode surface. The blood flow measuring apparatus is suitable for use in a cardiac pacemaker.

18 Claims, 3 Drawing Sheets

BLOOD FLOW MEASURING APPARATUS

BACKGROUND OF THE INVENTION

1. Field of the Invention

The present invention relates to a blood flow measuring apparatus of the type having a measuring electrode and a counter electrode intended to be brought into contact with the blood of a patient, and a measuring unit adapted to measure the voltage or current between the electrodes to determine therefrom the flow of blood.

2. Description of the Prior Art

There exist several methods of measuring the flow of body fluids. The flow can be measured by Doppler sound probes, dilution methods where the flow is determined from probe temperature changes, cf. e.g. U.S. Pat. No. 5,598,847.

In U.S. Pat. No. 5,602,342 a method and a device are proposed for determining the flow of an electrolytic fluid from the measured voltage or current between two stationary electrodes immersed in the electrolytic fluid. No specific design of the measuring electrodes is shown in this document, but only schematically shown electrodes are positioned in the fluid path.

SUMMARY OF THE INVENTION

An object of the present invention is to provide a blood flow measuring apparatus based on the measuring principle described in the above U.S. Pat. No. 5,602,342 which does not disturb the flow and is well suited for continuous flow measurements.

This object is achieved in an apparatus according to the invention wherein the measuring electrode surrounds the total flow in the body vessel in question. The measuring electrode is not positioned in the flow path as in the known flow measuring apparatus of this kind, thus avoiding disturbances of the flow. The measuring electrode of the apparatus according to the invention can be designed for location in any part of the human vascular system. Further, when using a point shaped electrode the measure result is dependent on the position of the electrode in the flow inside the vessel in question. This is avoided with the present invention by using a ring-shaped measuring electrode with a size adapted to the dimensions of the vessel. The counter electrode can be any type of electrode, also an electrode intended for other purposes, e.g. a pacemaker stimulation electrode. The only requirement on the counter electrode is that no other current than the measuring current must pass this counter electrode during the measuring period. The blood flow measuring apparatus according to the invention is especially well adapted for measuring changes in the flow from a certain normal or reference flow.

To facilitate transveneous movement of the ring-shaped electrode to its final position, the ring-shaped electrode preferably is designed to enable reduction of its diameter for the implantation procedure. One example of a technique for reducing the diameter for this purpose is the stent. In embodiments of the apparatus according to the present invention the ring-shaped electrode is foldable to enable reduction of its diameter for implantation. The ring-shaped electrode can be composed of several mutually foldable segments. Alternatively the ring-shaped electrode can be slotted, allowing it to be wound together so as to reduce the cross-section area for implantation.

To facilitate implantation the ring-shaped electrode in another embodiment of the apparatus according to the invention, is designed for introduction, in its folded or wound together state, into a catheter suitable for insertion into a blood vessel, and further is designated to be pressed out of the catheter by a stiff wire to then relax to its ring-shape.

In other embodiments of the apparatus according to the invention the ends of the ring-shaped electrode are flexible, preferably by forming a number of axial slits in the ends of the ring-shaped electrode or by providing the ends of the ring-shaped electrode with a wave-shape, the curvature of the wave-shape being small compared to the curvature of the ring. In this way the ends of the tube become soft so there will be no harmful cutting effect against the wall of the vessel from the ring-shaped electrode.

In other embodiments of the apparatus according to the invention, wherein a lead connects the ring-shaped electrode to the measuring unit, an elongated part of plastic material is attached to the ring-shaped electrode to extend along the lead to serve as a support therefor. The lead preferably passes through holes in the elongated part. This elongated part will serve as a mechanical relief to the lead. Because of the continuous moments of the implant every detail in the design must have an extreme fatigue durability and for this reason such a mechanical relief is of great importance.

DESCRIPTION OF THE PREFERRED EMBODIMENTS

Figure 1:
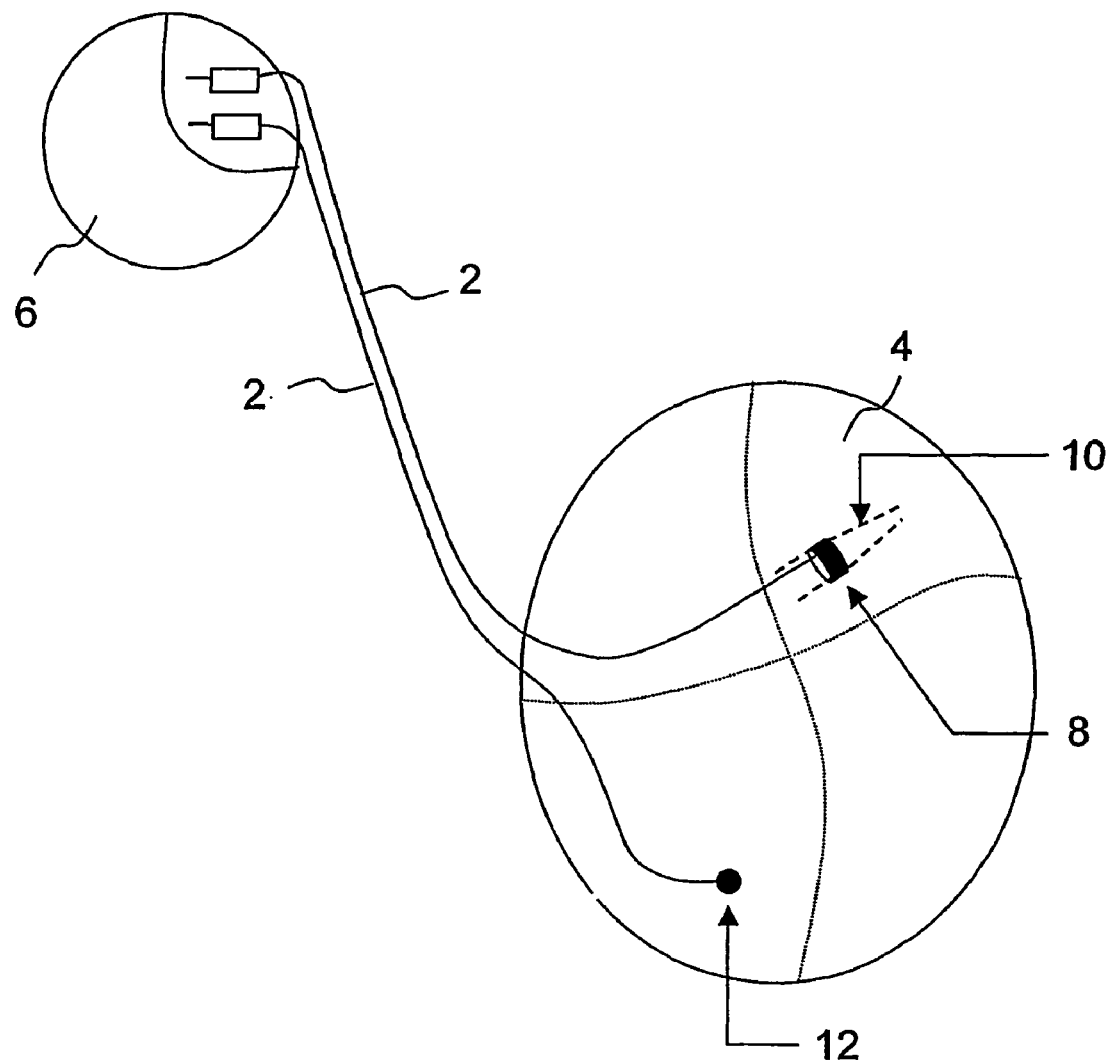
FIG. 1 schematically illustrates a pacemaker system provided with a blood flow measuring apparatus according to the invention.

FIG. 1 illustrates schematically a pacemaker system with leads 2 implanted into a heart 4. The leads 2 are connected to a pulse-generator and inside the pulse-generator housing 6 electronic circuitry of a flow measuring apparatus according to the invention is located. One of the leads 2 is connected to a ring-shaped measuring electrode 8 located in the coronary sinus vein 10. The other lead 2 is connected to an electrode 12 which can be used as a counter electrode in the measuring apparatus according to the invention but also be used for other purposes, e.g. supply of stimulation pulses from the pacemaker pulse generator to the heart 4. This counter electrode 12 must be in electrolytic contact with the measuring electrode.

Figure 2:
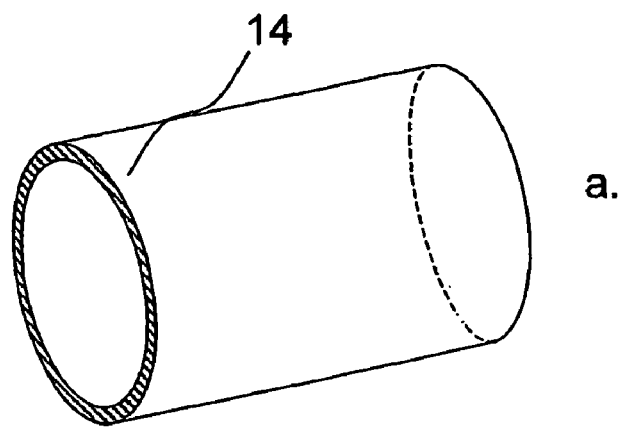
FIG. 2A shows a foldable ring-shaped electrode in a relaxed state.
FIG. 2B shows the foldable ring-shaped electrode of FIG. 2A in a folded state.
Figure 2:
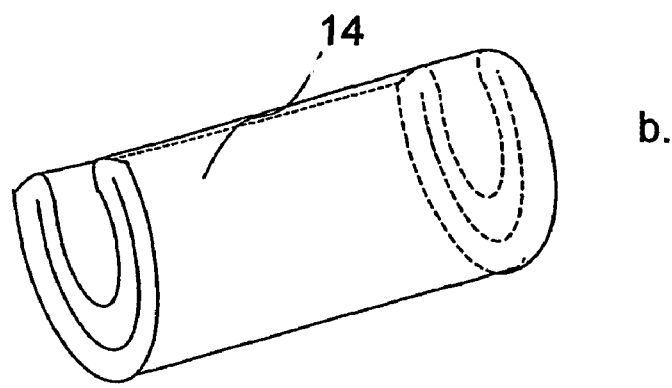

In FIG. 2A a ring-shaped electrode is shown in its expanded implanted state. The electrode 14 is made foldable and in FIG. 2B the electrode 14 is shown folded together to reduce its diameter for facilitating implantation from outside the patient's body through the vascular system.

Figure 3:
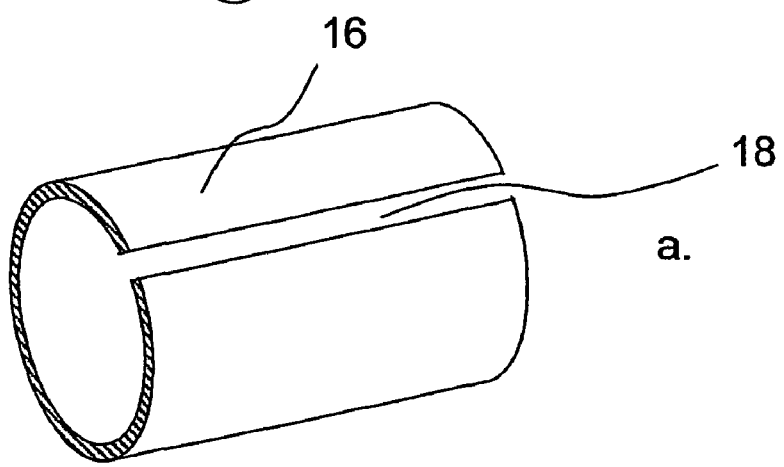
FIG. 3A shows a ring-shaped electrode having a longitudinal slit, in a relaxed state.
FIG. 3B shows the ring-shaped electrode of FIG. 3A in a wound together state.
Figure 3:
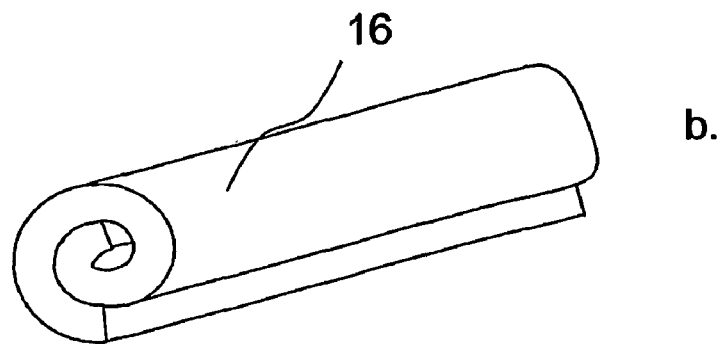

FIGS. 3A and 3B show an alternative embodiment of the ring-shaped measuring electrode 16 with a longitudinal slit 18 formed in the wall of the ring 16. In FIG. 3A the expanded state of the ring-shaped electrode 16 is shown and in FIG. 3B the slitted ring electrode is shown in a wound together state for reduction of its diameter to facilitate implantation.

Also other designs of the ring-shaped electrode are possible for making reduction of its diameter possible for the implantation. Thus the ring-shaped electrode can include a number of mutually foldable segments. The ring-shaped electrode can also be designed according to the so-called stent technique. The ring-shaped electrode then consists of a net or of a wound coil. During the implantation procedure the coil is comparably long and has a small diameter. The angle of the threads is low compared to the length during implantation. When the coil has reached its final position the coil is widened and shortened by drawing or pressing the two ends of the ring-shaped coil together or by using an inserted balloon. In this way the stent will fit to the inner side of the vessel.

Figure 4:
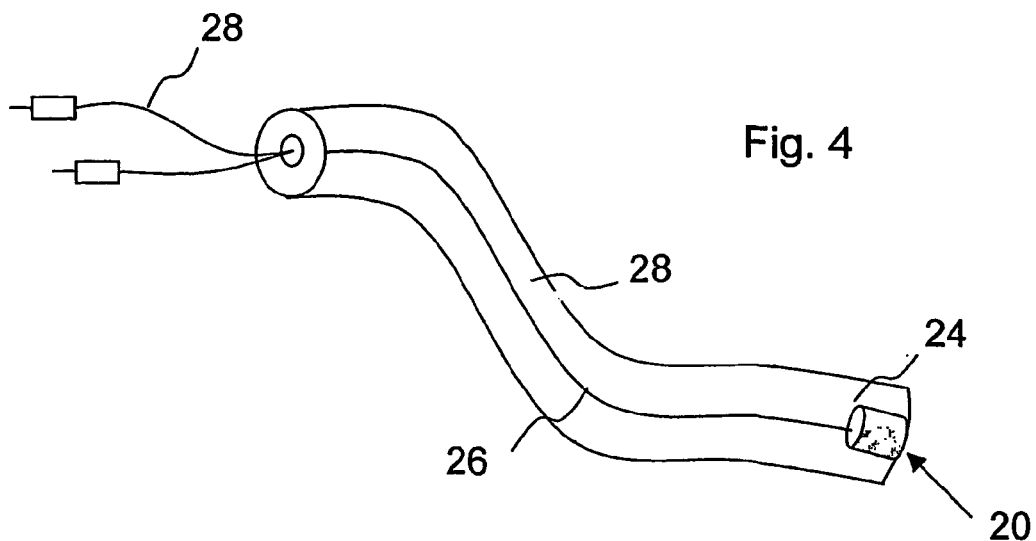
FIG. 4 schematically illustrates a catheter suitable for inserting the ring-shaped electrode into a body vessel.

As an alternative a tube-like catheter can be used for the implantation of the ring-shaped electrode into the vascular system. Such a catheter is illustrated in FIG. 4. The ring-shaped electrode is than folded together and inserted at the distal 20 of the catheter 22. The catheter 22 has a diameter and a length suitable for implantation from outside the patient's body through the vascular system. A stiff wire 26 is located in the catheter, and when the catheter 22 and the electrode 24 reach the desired position, which is preferably checked by X-raying, the stiff wire 26 is used to press the folded electrode 24 out of the catheter. When the electrode 24 is pressed out of the catheter 22 it will relax and assume its ring-shape, adapted to the size of the vessel in question. The catheter 22 is also provided with a longitudinal slit so the lead 28 can easily be taken out of the catheter 22 to allow the catheter 22 to be moved away from the lead 28.

Figure 5:
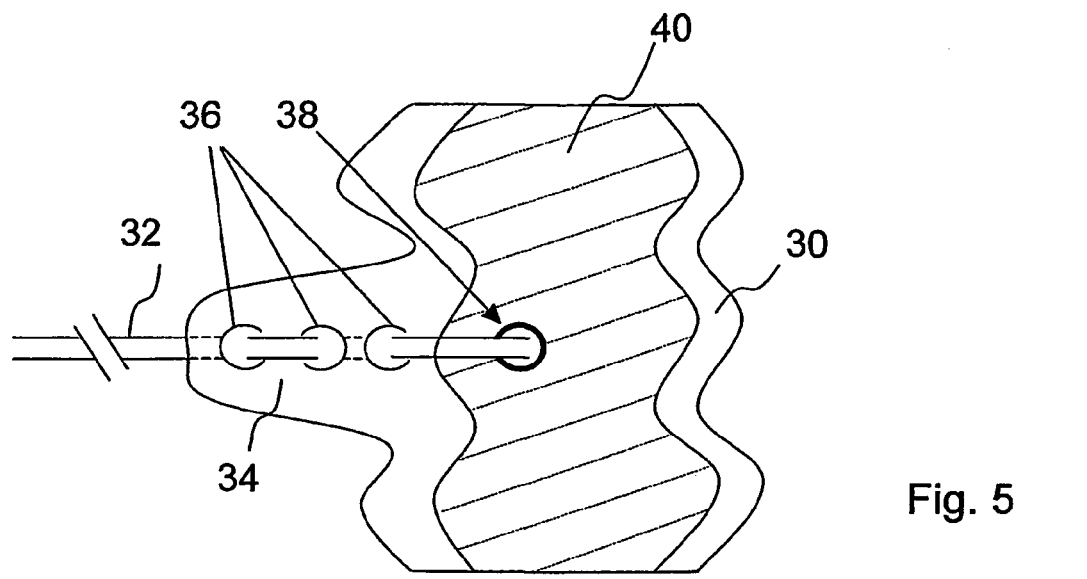
FIG. 5 shows a further embodiment of the ring-shaped electrode of the apparatus according to the invention, as seen from an interior surface of the ring electrode with the ring electrode flattened out.

To avoid cutting against the wall of the body vessels it is desirable to make the ends of the ring-shaped electrode soft. This can be provided by a number of axial slits formed in the ends of the ring-shaped electrode or by a wave-shape as illustrated in FIG. 5. Thus FIG. 5 shows a view from the inside of a ring-shaped electrode 30 slotted and flattened out. The ring exhibits a wave-shape with a curvature that is small compared to the curvature of the ring itself. In the figure the waves are shown in an enlarged scale. The wave-shape can designed such that some of the waves also tend to fold out to improve the fixation of the ring against the wall of the vessel.

Figure 6:
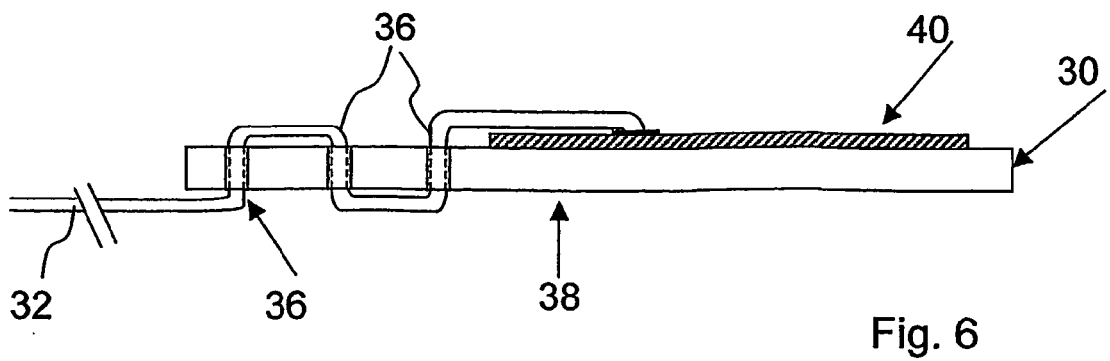
FIG. 6 is a side view, partly in section, of the embodiment of the ring-shaped electrode of FIG. 5.

The electrode 30 is connected by a lead 32 to its associated electronics located in e.g. a pacemaker pulse-generator housing as described above. The ring electrode 30, which is preferably made of a biological stable plastic covered on its interior surface by a metallic layer 40, metallic net or the like, is designed with an elongated supporting part 34 extending from the plastic of the ring 30. In the supporting part 34 a number of holes 36 is made through which the lead 32 passes, cf. also FIG. 6. Such a mechanical relief for the lead 32 is very important. Because of the continuous movements of every detail of this part of the apparatus according to the invention an extremely high fatigue durability is required.

Connections between different metal parts in this construction is preferably realized by laser welding. At 38 in FIGS. 5 and 6 the lead 32 is contacted to the active metallic electrode surface 40 by welding. However, other techniques like folding and pressing together different metal parts are possible. It is important that every connection between metal parts of the construction which may come into contact with body fluids must be protected against corrosion and measures must be taken to avoid influence on the measured values. Such a protection can be realized by applying a suitable plastic material, like e.g. spraying Teflon®, evaporating Parlene® or molded silicon rubber.

Although modifications and changes may be suggested by those skilled in the art, it is the invention of the inventor to embody within the patent warranted heron all changes and modifications as reasonably and properly come within the scope of his contribution to the art.

The invention claimed is:

1. A blood flow measuring apparatus comprising:
a measuring electrode and a counter electrode adapted for in vivo contact with blood of a patient;
said measuring electrode being ring-shaped and having a size and dimensions adapted to fit within a blood vessel of the patient, and having an inner surface forming an active measuring electrode surface; and
a measuring unit connected to said measuring electrode and to said counter-electrode for measuring an electrical quantity, selected from the group consisting of voltage and current, between said measuring electrode and said counter-electrode, and for determining a flow of blood dependent on said electrical quantity.

2. A blood flow measuring apparatus as claimed in claim 1 wherein said electrical quantity is current, and wherein said measuring unit maintains a constant voltage between said measuring electrode and said counter-electrode while measuring said current.

3. A blood flow measuring apparatus as claimed in claim 1 wherein said active surface of said measuring electrode is of a same order of magnitude in size as said counter-electrode.

4. A blood flow measuring apparatus as claimed in claim 1 wherein said ring-shaped electrode is comprised of plastic material, and comprising an electrically conducting electrode material at least partially coating said inner surface.

5. A blood flow measuring apparatus as claimed in claim 4 wherein said electrically conducting electrode material comprises a platinum foil attached to said inner surface.

6. A blood flow measuring apparatus as claimed in claim 1 wherein said measuring electrode has an outer surface, and comprising insulation covering said outer surface.

7. A blood flow measuring apparatus as claimed in claim 1 wherein said measuring electrode comprises a metal net.

8. A blood flow measuring apparatus as claimed in claim 1 wherein said measuring electrode is foldable to reduce a diameter of said measuring electrode for implantation.

9. A blood flow measuring apparatus as claimed in claim 8 wherein said measuring electrode is comprised of a plurality of mutually foldable segments.

10. A blood flow measuring apparatus as claimed in claim 8 further comprising a catheter adapted for insertion into the blood vessel, and a stylet insertable into said catheter, and wherein said measuring electrode, when folded for implantation, is insertable into said catheter and is adapted to be forced out of said catheter by said stylet, to re-assume said ring-shape.

11. A blood flow measuring apparatus as claimed in claim 1 wherein said measuring electrode has a slot allowing said measuring electrode to be wound together to reduce a cross-sectional area of said measuring electrode for implantation.

12. A blood flow measuring apparatus as claimed in claim 8 further comprising a catheter adapted for insertion into the blood vessel, and a stylet insertable into said catheter, and wherein said measuring electrode, when wound for implantation, is insertable into said catheter and is adapted to be forced out of said catheter by said stylet, to re-assume said ring-shape.

13. A blood flow measuring apparatus as claimed in claim 1 wherein said measuring electrode has flexible ends.

14. A blood flow measuring apparatus as claimed in claim 1 wherein said measuring electrode has opposite ends, with a plurality of axial slits in the respective opposite ends.

15. A blood flow measuring apparatus as claimed in claim 1 wherein said measuring electrode has opposite wave-shaped ends, with a curvature of the wave-shape of said opposite ends being small compared to a curvature of said ring-shape.

16. A blood flow measuring apparatus as claimed in claim 1 comprising an electrical lead connecting said measuring electrode to said measuring unit, and wherein said measuring electrode comprises an elongated plastic material part extending along said lead to support said measuring electrode.

17. A blood flow measuring apparatus as claimed in claim 16 wherein said elongated part has holes therein, and wherein said lead passes through said holes in said elongated part.

18. A cardiac pacemaker comprising:
pacing circuitry that generates pacing pulses;
an electrode lead adapted for implantation in a blood vessel and adapted for interaction with cardiac tissue to deliver said pacing pulses to said cardiac tissue; and
a blood flow measuring apparatus having a measuring electrode and a counter-electrode carried by said lead and adapted for contact with blood of a patient, said measuring electrode being ring-shaped and having a size and dimensions adapted to fit within the blood vessel, and having an inner surface forming an active measuring electrode surface; and
a measuring unit electrically connected to said measuring electrode and said counter-electrode via said lead for measuring an electrical quantity, selected from the group consisting of voltage and current, between said measuring electrode and said counter-electrode, and for determining a flow of blood dependent on said electrical quantity.

* * * * *